United States Patent [19]

Niesert et al.

[11] Patent Number: 5,776,658
[45] Date of Patent: Jul. 7, 1998

[54] SILICONE-COMPATIBLE PHOTOINITIATORS, AND PHOTOSENSITIVE MIXTURES COMPRISING THEM

[75] Inventors: Claus-Peter Niesert, Frankfurt, Germany; Georg Pawlowski, Tokyo, Japan; Willi-Kurt Gries, Wiesbaden, Germany; Klaus-Juergen Przybilla, Frankfurt, Germany

[73] Assignee: AGFA-Gevaert AG, Leverkusen, Germany

[21] Appl. No.: 536,738

[22] Filed: Sep. 29, 1995

[30] Foreign Application Priority Data

Oct. 4, 1994 [DE] Germany .................. 44 35 487.8

[51] Int. Cl.⁶ .................. G03F 7/075; C08J 3/28; C08G 77/06; C08G 77/18
[52] U.S. Cl. .................. 430/281.1; 522/40; 522/904; 522/905; 556/436; 556/427; 556/425; 544/69; 544/229; 546/14; 548/406; 548/110; 549/4; 549/214; 552/209
[58] Field of Search .................. 522/40, 904, 905; 430/281.1; 556/436, 427, 425; 544/69, 229; 546/14; 548/406, 110; 549/4, 214; 552/209; 525/475, 326.5

[56] References Cited

U.S. PATENT DOCUMENTS

| 3,865,588 | 2/1975 | Ohto et al. ............ 96/33 |
|---|---|---|
| 4,184,873 | 1/1980 | Noshiro et al. ............ 430/258 |
| 4,271,255 | 6/1981 | Cho et al. ............ 430/253 |
| 4,391,963 | 7/1983 | Shirahata ............ 528/37 |
| 4,467,082 | 8/1984 | Shirahata et al. ............ 528/43 |
| 4,960,746 | 10/1990 | Hüsler et al. ............ 502/153 |
| 5,059,512 | 10/1991 | Babich et al. ............ 430/281.1 X |
| 5,086,192 | 2/1992 | Kessel et al. ............ 556/9 |
| 5,147,901 | 9/1992 | Rutsch et al. ............ 522/42 |

FOREIGN PATENT DOCUMENTS

| 0 108 037 | 5/1984 | European Pat. Off. . |
|---|---|---|
| 0 129 443 | 12/1984 | European Pat. Off. . |
| 0 162 572 | 11/1985 | European Pat. Off. . |
| 0 269 573 | 6/1988 | European Pat. Off. . |
| 0 281 941 | 9/1988 | European Pat. Off. . |
| 028194/A2 | 9/1988 | European Pat. Off. ............ 522/40 |
| 0 598 545 | 5/1994 | European Pat. Off. . |
| 2 078 242 | 1/1982 | United Kingdom . |

OTHER PUBLICATIONS

Kakinchi et al., *Bulletin of the Chemical Society of Japan*, Jan. 1995, vol. 68, No. 1, pp. 62–83.
Gatechair et al., *Journal of Radiation Curing*, vol. 10, No. 3, Jul. 1983, pp. 4–18.
Derwent Publications, Ltd., AN 78-55676, and JP-A 53 071 199, published Jun. 24, 1978.
Mueller et al., "Plaste u. Kautschuk", vol. 34, pp. 183–190, 1987. (No English Translation).
Timpe et al., "Photvernetzung von Siliconen", Adhaesion, pp. 28–35, 1985. (No English Translation).
Mueller et al., "Photovernetzung von Siliconen–eine Technologie der Zu kunft", vol. 41, pp. 1131–1138, 1988.
Kosar, "Light–Sensitive Systems", J. Wiley & Sons, New York, pp. 4–5, 1965.

*Primary Examiner*—Cynthia Hamilton
*Attorney, Agent, or Firm*—Foley & Lardner

[57] ABSTRACT

Compounds of the general formula I: $(SIL-X-)_m IN$ (I), in which SIL is a radical of the formula $Si(R^1)(R^2)(R^3)$, where $R^1$ is an alkyl, haloalkyl or alkoxy radical of 1 to 8 carbon atoms, an alkenyl radical, an alkenyloxy or acyloxy radical of 2 to 8 carbon atoms, an aryl or aryloxy radical of 6 to 10 carbon atoms, or a dialkyl-, diaryl- or alkylarylmethyleneaminooxy radical having $C_1$–$C_4$-alkyl or $C_6$-aryl groups; and $R^2$ and $R^3$ are identical or different radicals with the meaning of $R^1$ or X—IN; X is a group $C_nH_{2n}$; IN is the radical of a compound which is active as a photoinitiator or photosensitizer and which has at least one carbonyl group located on an aromatic nucleus; m is a number from 1 to 4; and n is a number from 2 to 12, or of the formula II: $Si_o O_{o-1}(-X-IN)_p R^4_{2o+2-p}$ (II), in which $R^4$ is a radical with the meaning of $R^1$, and two or more radicals $R^4$ may be the same as or different from one another; o is a number from 2 to 20,000; and p is a number from 1 to o, and the symbols X and IN are as defined above, the group X being attached to an aromatic carbon atom which is positioned ortho to the carbonyl group of IN. The compounds are prepared by reacting a compound IN—H with a compound SIL—X' or a compound $Si_o O_{o-1}(-X')_p R^4_{2o+2-p}$ in the presence of a ruthenium compound. They are suitable as radical-forming photoinitiators or as photosensitizers in silicone-containing photopolymerizable mixtures, in particular for the production of waterless-printing planographic printing plates.

21 Claims, No Drawings

SILICONE-COMPATIBLE PHOTOINITIATORS, AND PHOTOSENSITIVE MIXTURES COMPRISING THEM

BACKGROUND OF THE INVENTION

1. Field of the Invention

The invention relates to compounds which are suitable as photoinitiators and to photosensitive mixtures which comprise these compounds, especially mixtures based on silicone resins and on the silicone rubbers derived from them. The present invention also relates to processes for producing the compounds.

2. Description of Related Art

The photoinduced polymerization of thin films is of great practical importance for numerous applications, for example, in the production of rapid-curing coatings, in the coating of paper, in the drying of printing inks or in the production of printing plates. In order to obtain sufficient sensitivity to light, the photosensitive mixtures generally contain photoinitiators. Frequently, however, the poor solubility of the photoinitiators in the photosensitive mixture often restricts their scope for application and their ability to be processed.

These solubility problems are particularly marked in the preparation of photosensitive mixtures based on silicones as binders or photosensitive polymers, which are employed in numerous areas of application (see e.g., U. Müller et al., Plaste u. Kautschuk 34 (1987) 183 or H. J. Timpe et al., Adhäsion 1985 (10) 28). Organic compounds such as photoinitiators have a tendency to separate out of mixtures with silicone (cf. e.g., U. Müller, H. J. Timpe, Kautschuk, Gummi, Kunststoffe, 41 (1988) 1131). The phase separation of photoinitiator and silicone is clearly visible, for example, in the preparation of thin silicone films which comprise photoinitiators and can be crosslinked in two stages, first thermally and then photochemically. Frequently, the photoinitiator exudes or separates out from the silicone layer or crystallizes therein after or even during thermal curing. In order to prevent this from occurring, it is generally desirable to increase the compatibility of photoinitiators with silicones.

Silicone-based materials which can be cured in two stages may find application, inter alia, in printing plates which are suitable for water-free offset printing. Thus, for example, DE-A 22 07 495 describes photocrosslinkable silicone layers as ink-repellent layers for water-free offset printing. DE-A 28 02 085 and DE-A 30 12 953 describe corresponding printing plates which are developed by mechanical separation of image and nonimage areas by the peel-apart method. In this case, the ink-repellent and simultaneously photosensitive layer is formed by photopolymerizable silicones.

In order to increase the compatibility of photoinitiators with silicones, the substitution of photoinitiators with silyl or siloxanyl radicals, which do not themselves carry any other reactive group, has been described (e.g., in U.S. Pat. No. 5,086,192 and in EP-A 162 572). Alternatively, EP-B 281 941 discloses photoinitiators which carry reactive groups via which they can be linked covalently with various polymers. Suitable substituents which enter into the process of the thermal curing of silicones are known from silicone chemistry, examples being trialkoxysilyl or triacetoxysilyl radicals which participate in the condensation crosslinking of silicone resins (see e.g., W. Noll, Chemie und Technologie der Silicone [Chemistry and technology of silicones], Verlag Chemie, Weinheim 1968; G. Körner, M. Schulze, J. Weis (eds.), Silicone, Chemie und Technologie [Silicones, chemistry and technology], Vulkan-Verlag, Essen 1989). However, a common disadvantage of the two approaches described above, is that the specifically substituted photoinitiators must be synthesized in complex, usually multistage reactions.

SUMMARY OF THE INVENTION

One object of the present invention is to provide photoinitiators or photosensitizers which have the capacity under the influence of light to initiate free-radical polymerization, which are compatible with silicones and which can be prepared in a single reaction step from known highly active photoinitiators or photosensitizers.

Another object of the present invention is to provide an improved process for the production of the photoinitiators or photosensitizers of the present invention. Still another object of the present invention is to provide a photosensitive mixture which includes the photoinitiators or photosensitizers of the present invention.

Yet another object of the present invention is to provide a printing plate for offset printing which is produced using the photoinitiators or photosensitizers of the present invention. Still another object of the present invention is to provide a composition which contains convalently bonded photoinitiators and photosensitizers of the present invention. Another object of the present invention is to provide a two-stage cured silicone rubber and a process for the two-stage curing.

In accomplishing the foregoing objectives there has been provided according to one aspect of the present invention compounds of the formula I $$(SIL—X—)_m IN \qquad (I),$$

in which

SIL is a radical of the formula $Si(R^1)(R^2)(R^3)$, where $R^1$ is an alkyl, haloalkyl or alkoxy radical of 1 to 8 carbon atoms, an alkenyl radical, an alkenyloxy or acyloxy radical of 2 to 8 carbon atoms, an aryl or aryloxy radical of 6 to 10 carbon atoms, or a dialkyl-, diaryl- or alkylaryl-methyleneaminooxy radical having $C_1$-$C_4$-alkyl or $C_6$-aryl groups, and $R^2$ and $R^3$ are identical or different radicals with the meaning of $R^1$ or X—IN, X is a group $C_n H_{2n}$, IN is the radical of a compound which has one or more of a photoinitiator or photosensitizer activity and which has at least one carbonyl group located on an aromatic nucleus, m is a number from 1 to 4, and n is a number from 2 to 12;

or a compound of the formula II $$Si_o O_{o-1}(—X—IN)_p R^4_{2o+2-p} \qquad (II)$$

in which $R^4$ is a radical as defined for $R^1$, and two or more radicals $R^4$ may be the same as or different from one another, o is a number from 2 to 20,000, and p is a number from 1 to o, and the symbols X and IN are defined as above, and the group X is attached to an aromatic carbon atom which is positioned ortho to the carbonyl group of IN.

According to another aspect of the present invention there has been provided a process for the preparation of the above-defined compounds, which comprises reacting a compound of the formula III $$IN-H, \quad (III)$$

in which the hydrogen atom is on an aromatic carbon atom positioned ortho to a carbonyl group, in the presence of a catalytic amount of a ruthenium compound, with a compound of the formula IV $$SIL-X' \quad (IV)$$

or a compound of the formula IVA $$Si_oO_{o-1}(-X')_pR^4{}_{2o+2-p} \quad (IVA)$$

in which X' is an ω-alkenyl radical of 2 to 12 carbon atoms and IN, SIL, $R^4$, o and p are defined as above.

The "catalytic amount" is in general an amount from 0.1 to 10.0 mole-%, preferably 0.2 to 5.0 mole-%, relative to IN—H.

According to still another aspect of the present invention, there has been provided a photosensitive mixture comprising:

a) a polysiloxane, b) a free-radically polymerizable compound having at least one terminal ethylenically unsaturated group, and c) a compound which forms radicals when irradiated with actinic light, and in which the radical-forming compound (c) is a compound of one of the above-defined formulae I and II.

According to yet another aspect of the present invention, there has been provided a printing plate for waterfree offset printing, which includes an area exposed to actinic radiation and an area not exposed to actinic radiation, wherein the exposed area comprises a substrate, a photopolymerized layer and a photopolymerized silicone layer which included one or both of compounds I and II according to the present invention, and wherein the nonexposed areas comprises the substrate, the photopolymerizable layer, and the photosensitive silicone layer, at least the photosensitive silicone layer being removable in a subesequent development step in which the ready-to-use printing plate is formed.

According to still another aspect of the present invention, there has been provided a composition, which includes one or both of compounds I and II according to the present invention, and which contains reactive silyl radicals covalently bonded to other compounds of corresponding reactivity.

According to still another aspect of the present invention, there has been provided a process for curing silicone, comprising crosslinking silicone resins, which contains at least one of the compounds I and II of the present invention, by a condensation reaction to produce a silicone rubber, and further polymerizing the silicone rubber by exposure to actinic radiation.

Further objects, features and advantages of the present invention will become apparent to those skilled in the art from a detailed description of preferred embodiments which follows.

DETAILED DESCRIPTION OF THE PREFERRED EMBODIMENTS

A structural requirement for the photoinitiators IN—H employed in the preparation of the compounds according to the present invention is the presence of an aryl ketone structural element in the molecule. At least one aromatic C—H group must be present in a position ortho to the carbonyl group. Various classes of photoinitiators or sensitizers are known which meet these requirements, examples being benzoin ethers and other benzoin derivatives, benzil ketals, hydroxyalkylphenones, α-aminoacetophenone derivatives, α-haloacetophenone derivatives, benzophenones, thioxanthones, anthraquinones or acridones. Other classes meeting these requirements can also be used according to the present invention.

It has recently been disclosed that certain aromatic ketones can be reacted, under the influence of ruthenium complexes, with olefins in such a way that the position on the aromatic nucleus which is ortho to the carbonyl group is alkylated by the olefin (see, S. Murai et al., Nature 366 (1993) 529 which is expressly incorporated by reference in its entirety) Examples of suitable olefin components are vinylsilanes. The ketone components specified therein are merely those compounds for which an action as photoinitiators is not known.

The present inventors have surprisingly found that this reaction can also be carried out if different substituents are present either in the aromatic or in the aliphatic moiety of the ketones, so that even complex compounds such as the above-mentioned photoinitiators can be reacted.

Surprisingly, the photosensitivity of the photo-initiators is largely retained despite the introduction of the silylalkyl substituent. The products of the reactions according to the present invention generally possess enhanced compatibility with silicones, or can intervene in the crosslinking of silicones. The silicone rubbers which can be prepared by this method are generally photosensitive.

The photoinitiators according to the present invention are preferably compounds in which IN is a radical of one of the formulae V and VI

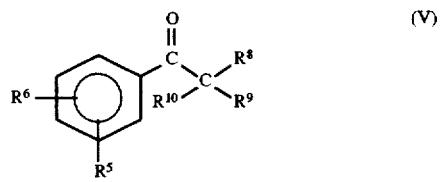

(V)

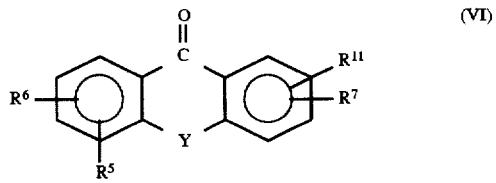

(VI)

in which $R^5$, $R^6$ and $R^7$ are identical or different and are hydrogen atoms, halogen atoms, phenyl, benzyl or benzoyl radicals, alkyl radicals of 1 to 12 carbon atoms, cycloalkyl radicals of 5 to 6 carbon atoms or radicals of the formulae $OR^{12}$, $SR^{12}$, $SOR^{15}$, $SO_2R^{15}$, $N(R^{13})(R^{14})$, $NH-SO_2-R^{15}$ or $NHCOR^{15}$, $R^8$ and $R^9$ are identical or different and are hydrogen atoms, alkyl radicals of 1 to 12 carbon atoms, alkenyl radicals of 2 to 12 carbon atoms, 5- or 6-membered cycloalkyl radicals, aralkyl radicals of 7 to 9 carbon atoms, $OR^{12}$, $CH_2OR^{12}$ or $N(R^{13})(R^{14})$, or $R^8$ and $R^9$ together with the carbon atom to which they are attached form a cycloaliphatic ring of 5 to 6 carbon atoms; and $R^{10}$ is a hydrogen atom, $OR^{12}$ or an aryl radical of 6 to 8 carbon atoms, or, alternatively, $R^8$, $R^9$ and $R^{10}$ together with the carbon atom to which they are attached form a substituted or unsubstituted benzene ring (it being understood in this case that these radicals individually are not hydrogen atoms or methyl groups), $R^{11}$ is X—SIL or $R^7$, and if $R^{11}$ is X—SIL it is in position 1 of the triple-ring system of the formula VI.

$R^{12}$ is a hydrogen atom, an alkyl radical of 1 to 12 carbon atoms, a 5- or 6-membered cycloalkyl radical or an alkanoyl radical of 2 to 13 carbon atoms.

$R^{13}$ and $R^{14}$ are identical or different and are hydrogen atoms, alkyl radicals of 1 to 12 carbon atoms or 5- or 6-membered cycloalkyl radicals, or $R^{13}$ and $R^{14}$ together with the nitrogen atom to which they are attached form a 5- or 6-membered heterocyclic ring which may contain O, S or N as additional heteroatoms, $R^{15}$ is an alkyl radical of 1 to 12 carbon atoms or an aryl radical of 6 to 10 carbon atoms, and Y is O, S, $NR^{12}$, $CH_2$, C(O) or a single bond, and if Y=C(O) radicals X—SIL may also be present in positions 4 and 5 of the triple-ring system.

If $R^8$, $R^9$ and $R^{10}$ and the carbon to which they are attached form a benzene ring, it may be substituted by, for example, halogen atoms, alkoxy groups of 1 to 8 carbon atoms or radicals $R^{15}$. Other suitable substituents may also be used according to the present invention.

The radicals $R^1$ and $R^2$ are preferably alkyl or alkoxy groups of 1 to 4 carbon atoms, especially 1 or 2 carbon atoms.

The ratio p:o is generally between 1:100 and 1:2, preferably in the range from 1:10 to 2:5.

$R^4$ is preferably an alkyl group of 1 to 4 carbon atoms, especially a methyl group.

X is a generally straight-chain or branched, substituted or unsubstituted alkylene group preferably of 2 to 6 carbon atoms, especially 2 to 4 carbon atoms.

If IN is a radical of the formula V, at least one of the radicals $R^5$ and $R^6$ is preferably a hydrogen atom. The other is preferably H, alkyl-, alkoxy- or alkylmercapto of 1 to 4 carbon atoms, especially of 1 or 2 carbon atoms, $N(R^{13})(R^{14})$ with alkyl radicals $R^{13}$ and $R^{14}$ of 1 to 4 carbon atoms each such as dimethylamino, diethylamino or dipropylamino, or a radical $N(R^{13})(R^{14})$ which is closed to form a heterocyclic ring having 5 or 6 members, and which preferably contains O,S or NH as additional heteroatoms such as morpholino, piperidino, piperazin-1-yl, pyrrol-1-yl or 2H-pyridin-1-yl.

If the radicals $R^8$ and $R^9$ are separate, at least one of them is preferably an alkyl or alkoxy group of 1 to 4 carbon atoms and preferably not more than one of them is a hydrogen atom, a hydroxy or aralkyl group, especially a benzyl group. The radical $R^{10}$ is preferably a substituted or unsubstituted phenyl radical, a hydroxyl group or a tertiary linear or cyclic amino group. Preference is also given to compounds in which $R^8$ and $R^9$ are linked to form a cycloaliphatic ring, or in which $R^8$, $R^9$ and $R^{10}$ and the carbon to which they are attached form a benzene ring.

In the formula VI, $R^5$, $R^6$ and $R^7$ are preferably hydrogen atoms. One or two of these radicals may preferably be halogen atoms, alkyl groups of 1 to 4 carbon atoms or tertiary amino groups of 2 to 6 carbon atoms, especially dialkylamino groups having 1 or 2 carbon atoms in the alkyl group.

Y is preferably O,S, NH or CO, especially S.

If $R^{12}$, $R^{13}$, $R^{14}$ and $R^{15}$ are alkyl radicals, they preferably have 1 to 6 carbon atoms, especially 1 to 3 carbon atoms. Preferred alkanoyl radicals are those having 2 to 4 carbon atoms.

Radicals containing alkyl radicals and/or alkyl groups in the context of the present invention are defined as meaning straight-chain or branched radicals which are unsubstituted or are substituted by halogen atoms or hydroxyl groups and whose chain may be interrupted by ether oxygen atoms.

The compounds according to the invention are generally prepared from known starting ketones IN—H which are generally active themselves as photoinitiators or photosensitizers. "Active as photoinitiators or photosensitizers" means that the compounds upon exposure to irradiation form a chemically active species, normally free radicals, or transfer the irradiation energy to another compound which is thereby sensitized and induced to form such species (see e.g. J. Kosar, Light-Sensitive Systems, J. Wiley & Sons, New York [1965] p.5). Examples of suitable starting compounds are benzoin derivatives, such as benzoin, benzoin methyl ether, benzoin ethyl ether, benzoin isopropyl ether, benzoin acetate; benzil derivatives such as benzil dimethyl ketal; a-aminoalkyl phenyl ketones, for example, those described in EP-A 287 561 or 88 050; and hydroxyalkyl phenyl ketones, for example, those described in DE-C 27 22 264 or EP-B 3002. All of the above references are hereby incorporated by references in their entireties. Also suitable are thioxanthone derivatives such as thioxanthone, 2-isopropylthioxanthone, 3-methylthioxanthone, 2-chlorothioxanthone, 2,4-dichlorothioxanthone and 1,7-dichloro-4-methylthioxanthone; anthraquinone derivatives such as anthraquinone, 2-methylanthraquinone, 2-ethylanthraquinone, 1-chloroanthraquinone and 1,8-dichloroanthraquinone; or acridones such as 9(10H)-acridone, 10-methyl-9(10H)-acridone, 2-dimethylamino-9 (10H)-acridone and 10-butyl-2-chloro-9(10H)-acridone.

The compounds of the formulae I and II according to the present invention are prepared by reacting the aromatic ketones IN—H (III) with compounds of the type SIL—X' (IV), in which SIL is as defined above, i.e., a radical $Si(R^1R^2R^3)$ or compounds of the formula II which can be a polymer chain.

The reaction generally takes place under the action of suitable catalysts, especially ruthenium compounds as described by Murai et al. [Nature 366 (1993) 529]. A compound which has proven particularly suitable in this context is $RuH_2(CO)(PPh_3)_3$. The components are generally mixed in an inert solvent such as toluene, benzene, xylene, chlorobenzene or an aliphatic, unsubstituted or halogenated hydrocarbon, and brought to reaction at elevated temperature, preferably under a protective gas. In this case the reaction temperature is generally between 50° and 250° C., preferably between 100° C. and 180° C., and is most preferably the reflux temperature of the solvent used. It is particularly preferred to use toluene at reflux temperature. The reaction can be monitored by gas chromatography or thin-layer chromatography. The product can be worked up and purified by the conventional methods known to those skilled in the art using the present disclosure as a guide, especially by distillation or by chromatography.

Examples of photoinitiators according to the invention are the following compounds:

2-[2-(Trimethoxysilyl)ethyl]benzoin methyl ether (1),
2-[2-(Trimethoxysilyl)ethyl]benzoin ethyl ether (2),
2-[2-(Trimethoxysilyl)ethyl]benzoin isopropyl ether (3),
2-[2-(Triethoxysilyl)ethyl]benzoin isopropyl ether (4), 2-[2-(Trimethoxysilyl)ethyl]benzil dimethyl ketal (5),
1-Hydroxy-1-[2-(2-trimethoxysilylethyl)benzoyl]-cyclohexane (6),
2-Methyl-1-[4-methylthio-2-(2-trimethoxysilylethyl)phenyl]-2-morpholino-1-propanone (7),
-2-Methyl-1-[4-methylthio-2-(2-triethoxysilylethyl)phenyl]-2-morpholino-1-propanone (8)
2-Benzyl-2-dimethylamino-1-[2-(2-trimethoxysilylethyl)-4-morpholinophenyl]-1-butanone (9),
2-Benzyl-2-dimethylamino-1-[2-(2-triethoxysilylethyl)-4-morpholinophenyl]-1-butanone (10),
2-Benzyl-2-dimethylamino-1-[2-(2-trimethoxysilylpropyl)-4-morpholinophenyl]-1-butanone (11),
1-(2-Trimethoxysilylethyl)thioxanthone (12),
1,8-Bis-(2-trimethoxysilylethyl)thioxanthone (13),
2-Isopropyl-8-(2-trimethoxysilylethyl)thioxanthone (14),
2-Isopropyl-1,8-bis-(2-trimethoxysilylethyl)thioxanthone (15),
2-Benzyl-2-dimethylamino-1-[2-(2-(methyl-bis(trimethylsilyloxy)silyl)ethyl)-4-morpholinophenyl]-1-butanone (16),
Siloxane copolymer comprising dimethylsiloxane, methylvinylsiloxane and {2-[2-(2-benzyl-2-dimethylaminobutanoyl)-5-morpholinophenyl]ethyl}methylsiloxane units (17), and
2-[2-(2-Benzyl-2-dimethylaminobutanoyl)-5-morpholinophenyl]ethyl-terminated polydimethylsiloxane (18).

In accordance with the present invention, the photoinitiators or photosensitizers of the formulae I and II are preferably used in photosensitive mixtures which usually comprise a large number of components. However, the photoinitiators or photosensitizers can be used in other mixtures. Owing to the substitution with silylalkyl radicals, the compounds according to the present invention possess superior properties in relation to the starting compounds, particularly, enhanced solubility in silicone mixtures, or, via a reactive silylalkyl group, are able to participate in the curing of silicones (condensation or addition crosslinking). In the latter case, the initiators are generally anchored covalently in the silicone network in the course of formation of a silicone rubber, thereby reducing or totally preventing the possibility of exudation and the diffusion of the initiator in the mixture. In the case of compounds substituted by unreactive silylalkyl radicals, the solubility in or compatibility with polysiloxane is increased, thereby reducing or eliminating the risk of phase separation between initiator/sensitizer and polysiloxane. At the same time, the tendency toward diffusion is reduced owing to large silyl or oligopolysiloxane radicals. A preferred application of the compounds according to the present invention, therefore, is their addition to photosensitive silicone mixtures.

Photosensitive silicone mixtures according to the present invention generally contain, in addition to at least one of the photoinitiators or photosensitizers according to the invention, reactive silicones which can be generally subjected to free-radical polymerization or crosslinking. Corresponding reactive substituents are, for example, acrylate or methacrylate radicals, vinylsilane groups in conjunction with mercapto-containing siloxanes, and polysiloxanes containing maleimide or vinyl ether groups. Other reactant substituents known to those skilled in the art can also be used. These radicals are generally linked via alkylene groups to the polysiloxane framework. If desired, free-radically polymerizable compounds which are not based on silicones can also be added to the silicone mixtures.

In addition, a range of additional components may be added to the polysiloxane mixtures. These additional components may include silicone crosslinking agents such as alkoxy-, acetoxy- or dialkylmethylene-aminooxysilane derivatives, such as dimethyldiethoxysilane, N-(2-aminoethyl)-3-aminopropyltrimethoxysilane, 3-methacryloyloxypropyltrimethoxysilane, (3-glycidyloxypropyl)trimethoxysilane, bis(N-methylbenzylamido)ethoxymethylsilane, vinyltrimethoxysilane, vinyltriacetoxysilane and methyltris(methylethylmethylene-aminooxy)silane for mixtures which can be crosslinked by condensation, or siloxanes which are generally substituted by vinyl groups or hydrogen atoms for mixtures which can be crosslinked by addition.

The mixtures may also comprise crosslinking catalysts, such as compounds of tin, zinc or platinum. Further photocatalysts, inhibitors, heat stabilizers, light stabilizers or photosensitizers, which may if desired also carry silyl substituents, may also be included in the mixtures. Colorants or fillers, such as calcium carbonate, titanium dioxide or silicon dioxide, may likewise be present, as may solvents or further additives.

A particular advantage of such mixtures according to the present invention lies in the possibility of carrying out curing in 2 stages. First of all, the mixture of the silicone resin can be converted to a crosslinked silicone rubber by the reactions which are conventional in the case of silicones, such as condensation or addition. The silicone rubber preferably contains the photoinitiators according to the present invention in dissolved form (in the case of nonreactive silylalkyl substituents) or in covalently bonded form (when reactive silylalkyl substituents are used). A silicone rubber of this type has the advantage of increased storage stability over a silicone rubber in combination with conventional photoinitiator. If the silicone rubber contains not only the photoinitiators but also compounds which may be polymerized by a free-radical reaction, then exposure—imagewise if desired—in a second polymerization step, which is in this case induced by light, may bring about further curing of the film. By means of the polymerization reaction, however, it is also possible to bring about specific alterations in the forces of cohesion within the film and, if an appropriate system of films is used, the forces of adhesion to adjacent films.

The possibility of curing silicones in 2 steps, a thermal step and a subsequent photochemical step, renders such silicone mixtures of particular interest for use in printing plates, especially those intended for water-free offset printing. These can be developed by peeling apart the support from the cover film (peel-apart technique) and separating the image and nonimage areas of the recording layer. A printing plate for water-free offset printing has ink-repellent regions, which generally consist of silicone material or of fluorinated polymers, and ink-accepting regions, consisting, for example, of organic polymers or of the exposed substrate surface.

In a typical example, a printing plate for water-free offset printing which can be developed by the peel-apart technique generally consists of a substrate material, for example, an aluminum plate, a metal plate or a plastic film, on which there is located a photopolymerizable layer. This layer generally carries a photosensitive silicone layer which comprises a crosslinked silicone rubber. On this silicone layer in turn is a protective and peel film which possesses a certain degree of adhesion to the silicone layer. Suitable adhesion and auxiliary layers may supplement the multilayer structure. By exposure, the photosensitive silicone layer and the underlying photopolymerizable layer are cured in an imagewise fashion, in the course of which the cohesive forces within the silicone layer increase but the adhesion to the photopolymer layer is also increased. The result of this is that when the film is peeled off (peel-apart development), the silicone layer is separated from the film in the exposed area and remains on the substrate, while the silicone layer in the unexposed area is removed with the peel film. In the exposed area, the printing plate then repels printing ink, while the photo polymerizable layer laid bare in the unexposed region accepts the printing ink. Printing plates of this generic type are described, for example, in EP-A 530 674 and in DE-A 27 25 762 both of which are expressly incorporated by reference in their entireties.

In addition to their use in silicone mixtures, the compounds according to the present invention can also be employed in other photosensitive mixtures. In general, such photosensitive mixtures contain not only the initiators according to the invention but also a polymeric binder, often as the principal component. Since radicals are produced in the course of photolysis of the initiator used, free-radically polymerizable, ethylenically unsaturated compounds are as a general rule added to the mixture in order to obtain a photo-induced increase in the molecular weight, or crosslinking. Such compounds are preferably acrylic or methacrylic acid and their derivatives, for example, pentaerythritol triacrylate, ethylene glycol diacrylate or polyethylene glycol dimethacrylate, maleic anhydride, maleamides, styrene compounds, vinyl ethers or vinyl esters. Other suitable free-radically polymerizable ethylenically unsaturated compounds may also be used. Further photoinitiators, photosensitizers, antioxidants such as organic amines, phosphines or allyl compounds, and chain transfer agents such as, for example, thiols, thiophenols or peroxides, can be added to the photosensitive mixtures. It is also possible to add dyes, antihalation agents, fillers such as silicic acid, calcium carbonate or gypsum, plasticizers such as glycol derivatives or alkyl phthalates, and surface-active substances. In addition to solvents it is also possible to add further auxiliaries which are conventional in the art.

Particular advantages arise from the possibility of the covalent linking of compounds according to the present invention containing reactive silyl radicals to other compounds of corresponding reactivity, especially polymers. When this is done, the photoinitiator and, if appropriate, the elimination products of photolysis are fixed in a stationary fashion.

Photoinitiators comprising reactive silylalkyl groups, for example, alkoxysilylethyl groups, can be linked covalently to appropriately reactive surfaces, especially to oxidic surfaces (glass, oxidic metal surfaces). In this way, high local concentrations of einitiator can be obtained by covering the surfaces with the compounds described herein. This is particularly advantageous if it is intended to carry out a photopolymerization reaction in order to achieve a high degree of adhesion of a photopolymer to a surface pretreated in this way, or to graft polymers onto the surface.

The proportion of the photoinitiators or photosensitizers according to the present invention in the photosensitive mixtures is generally 0.1–30%, preferably 0.2–15%. The remainder generally consists wholly or predominantly of polysiloxane. The exposure of the mixtures is carried out in the wavelength range which is typical for the respective class of compound. Typically, the light used has wavelengths of 200–600 nm, preferably 250–500 nm.

The examples which follow are intended to illustrate the invention. More detailed preferred embodiments regarding the preparation of the compounds described can be found in Synthesis Examples 1 to 16. Examples 17 to 20 describe the application of the substituted photoinitiators in photosensitive mixtures, especially those based on photosensitive silicone rubbers.

The synthesis of $RuH_2(CO)$ $(PPh_3)_3$ was carried out by known methods starting from commercial $RuCl_3$.aq (J. J. Levison, S. D. Robinson, J. Chem. Soc. (A) 1970, 2947–54, hereby incorporated by reference in its entirety). The catalyst can generally be employed in crude form (without chromatographic purification) without any adverse effect on its action. The reactions of olefins with aryl ketone photoinitiators with catalysis by $RuH_2(CO)$ $(PPh_3)_3$ were carried out under protective gas (argon or $N_2$) and with the exclusion of light. Sampling was carried out through a septum, and the reactions were monitored by thin-layer chromatography (silica gel, heptane/ethyl acetate mixtures).

In the nuclear magnetic resonance data given in the following examples, the abbreviations have the following meanings:

s=singlet; s(br)=singlet (broad); m=multiplet; mc=centered multiplet; t=triplet; d=doublet; dd=doublet of a doublet; q=quartet; hept=septet; hex= sextet; J=coupling constant; $H^1$, $H^2$ . . . =H at carbon atom 1, 2 . . .

EXAMPLE 1

Preparation of 2-[2-(trimethoxysilyl)ethyl]benzoin methyl ether (1)

4.52 g (20 mmol) of benzoin methyl ether, 3.36 ml (22 mmol) of vinyltrimethoxysilane, 367 mg (0.4 mmol) of $RuH_2(CO)$ $(PPh_3)_3$ and 30 ml of anhydrous toluene were mixed and stirred at reflux for 8 hours. Then a further 2 ml (13 mmol) of vinyltrimethoxysilane were added, stirring at reflux was continued for 2 hours, and the mixture was left to stand overnight. After addition of a further 400 mg (0.4 mmol) of $RuH_2(CO)$ $(PPh_3)_3$, stirring at reflux was continued for 9 hours, then the mixture was concentrated and worked up by chromatography (silica gel, $CH_2Cl_2$ or $CH_2Cl_2$/ethyl acetate). 490 mg of a yellowish oil were obtained. $^1$H-NMR ($CDCl_3$): 0.76 ppm (2H, mc, Et-$H^2$|$CH_2$ on the Si|); 2.60 ppm (2H, mc, Et-$H^1$ |$CH_2$ on the benzene nucleus]; 3.45 ppm (3H, s, $OCH_3$); 3.54 ppm (9H, s, $Si(OCH_3)_3$); 5.40 ppm (1H, s, benzoin-H); 7.16–7.72 ppm (8H, m, Ph-H); 7.50 ppm (1H, mc, Ph-$H^6$).

EXAMPLE 2

Preparation of 2-[2-(trimethoxysilyl)ethyl]benzoin ethyl ether (2)

12.01 g (50 mmol) of benzoin ethyl ether, 8.4 ml (55 mmol) of vinyltrimethoxysilane, 918 mg (1 mmol) of $RuH_2$ $(CO)$ $(PPh_3)_3$ and 80 ml of anhydrous toluene were mixed and stirred at reflux for 2 hours. A further 330 mg (0.4 mmol) of $RuH_2(CO)$ $(PPH_3)_3$ were then added, and the mixture was stirred at ref lux once more for 5 hours, concentrated and worked up by chromatography (silica gel, $CH_2Cl_2$ or $CH_2Cl_2$/ethyl acetate, ethyl acetate). 10.8 g of a brown oil were obtained which after distillation in a bulb tube (190° C., 0.03 mbar) gave 9.7 g (50%) of a yellowish oil. $^1$H-NMR ($CDCl_3$): 0.58–0.95 ppm (2H, mc, Et-$H^2$); 1.28 ppm (3H, t, OET-$CH_3$); 2.61 ppm (2H, mc, Et-$H^1$); 3.53 ppm (9H, s, $Si(OCH_3)_3$); 3.60 ppm (2H, mc, OEt-$CH_2$); 5.50 ppm (1H, s, benzoin-H); 7.15–7.37 ppm (8H, m, Ph-H); 7.51 ppm (1H, dd, Ph-$H^6$).

EXAMPLE 3

Preparation of 2-[2-(trimethoxysilyl)ethyl]benzoin isopropyl ether (3)

10.17 g (40 mmol) of benzoin isopropyl ether, 6.7 ml (44 mmol) of vinyltrimethoxysilane, 335 mg (0.4 mmol) of RuH$_2$(CO) (PPh$_3$)$_3$ and 75 ml of anhydrous toluene were mixed and stirred at reflux for 2 hours. At intervals of 2 hours, a further 3×200 mg (0.2 mmol) of RuH$_2$(CO) (PPh$_3$)$_3$ were added. The mixture was left to stand overnight, a further 200 mg (0.2 mmol) of RuH$_2$(CO) (PPh$_3$)$_3$ and 1 ml (6.6 mmol) of vinyltrimethoxysilane were added, the mixture was stirred at reflux for 8 hours, concentrated and worked up by chromatography (Florisil or silica gel, CH$_2$Cl$_2$/ethyl acetate/heptane mixtures). 10.6 g of oil were obtained which after distillation in a bulb tube (220° C., 0.08 mbar) gave 9.0 g (56%) of a yellowish oil. $^1$H-NMR (DCDl$_3$): 0.61–0.96 ppm (2H, mc, Et-H$^2$); 1.21 ppm (6H, d, isopropyl-CH$_3$, $^3$J$_{H,H}$=6.2 Hz); 2.61 ppm (2H, mc, Et-H$^1$); 3.53 ppm (9H, s, Si(OCH$_3$)$_3$); 3.71 ppm (1H, hept, sec. isopropyl-H); 5.55 ppm (1H, s, benzoin-H); 7.14–7.39 ppm (8H, m, Ph-H); 7.51 ppm (1H, dd, Ph-H$^6$)

EXAMPLE 4

Preparation of 2-[2-(triethoxysilyl)ethyl]benzoin isopropyl ether (4)

10.2 g (40 mmol) of benzoin isopropyl ether, 9.2 ml (44 mmol) of vinyltriethoxysilane and 735 mg (0.8 mmol) of RuH$_2$(CO) (PPh$_3$)$_3$ were dissolved in 60 ml of anhydrous toluene and degassed by passing in argon for ½ hour. The mixture was then stirred with exclusion of light and under argon, at reflux, for 7 hours and left to stand overnight at room temperature, a further 370 mg (0.4 mmol) of RuH$_2$(CO) (PPh$_3$)$_3$ and 1 ml (5 mmol) of vinyltriethoxysilane were added, and heating at reflux was carried out for a further 6.5 hours. After the toluene had been distilled off, the mixture was chromatographed on silica gel (initially heptane/CH$_2$Cl$_2$9:1, then CH$_2$Cl$_2$, then CH$_2$Cl$_2$/ethyl acetate, finally ethyl acetate) and purified by bulb-tube distillation. 9.8 g (55%) of a pale yellowish oil were obtained. $^1$H-NMR (CDCl$_3$): 0.61–0.95 ppm (2H, mc, Et-H$^2$); 1.21 ppm (6H, d, isopropyl-CH$_3$, $^3$J$_{H,H}$=6.0 Hz); 1.22 ppm (9H, t, ethoxy-CH$_3$, $^3$J$_{H,H}$=7.0 Hz); 2.61 ppm (2H, mc, Et-H$^1$); 3.71 ppm (1H, hept, isopropyl-H); 3.79 ppm (6H, q, ethoxy-CH$_2$); 5.55 ppm (1H, s, benzoin-H); 7.13–7.38 ppm (8H, m, Ph-H); 7.48 ppm (1H, dd, Ph-H$^6$, $^3$J$_{H^5,H^6}$=7.6 Hz).

EXAMPLE 5

Preparation of 2-[2-(trimethoxysilyl)ethyl]benzil dimethyl ketal (5)

5.12 g (20 mmol) of benzil dimethyl ketal, 3.36 ml (22 mmol) of vinyltrimethoxysilane and 367 mg (0.4 mmol) of RuH$_2$(CO) (PPh$_3$)$_3$ were dissolved in 30 ml of anhydrous toluene and stirred at reflux for 3 hours. After addition of a further 190 mg (0.2 mmol) of RuH$_2$(CO) (PPh$_3$)$_3$, the product was concentrated and chromatographed (silica gel, CH$_2$Cl$_2$/ethyl acetate mixtures). 1.6 g of a brownish oil were obtained which after bulb-tube distillation gave 1.4 g (17%) of a pale yellowish product. $^1$H-NMR (CDCl$_3$): 0.92 ppm (2H, mc, Et-H$^2$); 2.50 ppm (2H, mc, Et-H$^1$), 3.29 ppm (6H, s, OCH$_3$); 3.53 ppm (9H, s, Si(OCH$_3$)$_3$); 7.09 ppm (1H, mc)+7.20 ppm (1H, dd)+7.27–7.36 ppm (4H, m)+7.49–7.54 ppm (2H, m, Ph-H) and 7.60 ppm (1H, dd, Ph-H$^6$).

EXAMPLE 6

Preparation of 1-hydroxy-1-[2-(2-trimethoxysilylethyl)benzoyl]cyclohexane (6)

14.4 g (70 mmol) of 1-hydroxy-1-benzoylcyclohexane, 11.75 ml (77 mmol) of vinyltrimethoxysilane and 1.28 g (1.4 mmol) of RuH$_2$(CO) (PPh$_3$)$_3$ in 100 ml of anhydrous toluene were stirred at reflux for 4.5 hours. Following concentration and chromatography (silica gel, CH$_2$Cl$_2$/ethyl acetate), 12.2 g (49%) of a yellowish oil were obtained which was found to be pure by 1H-NMR spectroscopy but which was purified further by bulb-tube distillation (200° C., 0.2 mbar). $^1$H-NMR (CDCl$_3$):1.01 ppm (2H, mc, Et-H$^2$); 1.15–1.28 ppm (1H, m, cyclohexyl-H); 1.57–1.89 ppm (9H, m, cyclohexyl-H); 2.59 ppm (2H, mc, Et-H$^1$); 3.33 ppm (1H, s, OH); 3.35 ppm (9H, s, Si(OCH$_3$)$_3$); 7.17–7.40 ppm (4H, M, Ph-H).

EXAMPLE 7

7 Preparation of 2-methyl-1-[4-methylthio-2-(2-trimethoxysilylethyl)phenyl]-2-morpholino-1-propanone (7)

11.18 g (40 mmol) of 2-methyl-1-(4-methylthiophenyl)-2-morpholino-1-propanone, 735 mg (0.8 mmol) of RuH$_2$(CO)(PPh$_3$)$_3$ and 7.3 ml (48 mmol) of vinyltr 60 ml of anhydrous toluene were degased with argon for ½ hour and boiled at reflux for 5 hours. After standing overnight, boiling was repeated for 4 hours, then 360 mg (0.4 mmol) of RuH$_2$(CO)(PPh$_3$)$_3$ and 2 ml (13 mmol) of vinyltrimethoxysilane were added, and the mixture was stirred at reflux for a further 5 hours. Concentration and chromatography (silica gel, CH$_2$Cl$_2$/ethyl acetate) gave 3.04 g (18%) of a yellowish oil. $^1$H-NMR (CDCl$_3$): 1.01 ppm (2H, mc, Et-H$^2$); 1.22 ppm (6H, s, Pr-H$^3$, CH$_3$); 2.50 ppm (3H, s, -SCH$_3$); 2.58 ppm (4H, mc, *morpholine—O—CH$_2$); 2.69 ppm (2H, mc, Et-H$^1$); 3.59 ppm (9H, s, Si(OCH$_3$)$_3$); 3.70 ppm (4H, mc, **morpholine—N—CH$_2$); 7.03 ppm (1H, dd, Ph-H$^5$, $^3$J$_{H^5,H^6}$=8.4 Hz, $^4$J$_{H^3,H^5}$=2.0 Hz); 7.11 ppm (1H, d, Ph-H$^3$); 8.47 ppm (1H, d, Ph-H$^6$).

*protons on the morpholine—C-3 and C-5
**protons on the morpholine—C-2 and C-6

EXAMPLE 8

Preparation of 2-methyl-1-[4-methylthio-2-(2-triethoxysilylethyl)phenyl]-2-morpholino-1-propanone (8)

11.18 g (40 mmol) of 2-methyl-1-(4-methylthiophenyl)-2-morpholino-1-propanone, 735 mg (0.8 mmol) of RuH$_2$(CO) (PPh$_3$)$_3$ and 10.0 ml (48 mmol) of vinyltriethoxysilane in 60 ml of anhydrous toluene were degase with argon for ½ hour and boiled at reflux for 50 hours. Concentration and chromatography (silica gel, CH$_2$Cl$_2$/ethyl acetate) gave 1.02 g (6%) of a yellowish oil. $^1$H-NMR (CDCl$_3$): 0.99 ppm (2H, mc, Et-H$^2$); 1.22 ppm (6H, s, CH$_3$); 1.24 ppm (9H, t, CH$_3$ of Si(OEt)$_3$); 2.50 ppm (3H, s, SCH$_3$); 2.59 ppm (4H, mc, morpholine-N—CH$_2$); 2.69 ppm (2H, mc, Et-H$^1$); 3.70 ppm (4H, mc, morpholine-O—CH$_2$); 3.85 ppm (6H, q, SiOCH$_2$, $^3$J$_{H,H}$=6.8 Hz); 7.03 ppm (1H, dd, Ph-H$^5$, $^3$J$_{H^5,H^6}$=8.2 Hz, 4J$_{H^3,H^5}$=2.0 Hz); 7.13 ppm (1H, d, Ph-H$^3$); 8.40 ppm (1H, d, Ph-H$^6$).

EXAMPLE 9

Preparation of 2-benzyl-2-dimethylamino-1-[2-(2-trimethoxysilylethyl)-4morpholinophenyl]-1-butanone (9)

14.6 g (40 mmol) of 2-benzyl-2-dimethylamino-1-(4-morpholinophenyl)-1-butanone, 750 mg (0.8 mmol) of RuH$_2$(CO) (PPh$_3$)$_3$ and 13.4 ml (88 mmol) of vinyltrimethoxysilane were dissolved in 50 ml of toluene and degased using N$_2$. After heating with stirring at reflux for 41 hours, the solvent was distilled off and the product was chromatographed (silica gel, $CH_2Cl_2$/ethyl acetate). 13.8 g (67%) of dark red oil were obtained which were purified by boiling in heptane with active charcoal followed by filtration to give a yellow, viscous oil. $^1$H-NMR ($CDCl_3$): 0.61 ppm (3H, t, Bu-H$^4$, $^3J_{H,H}$=7.2 Hz); 1.2 ppm (2H, mc, Et-H$^2$); 1.88 ppm (2H, mc, Bu-H$^3$); 2.37 ppm (6H, s, N(CH$_3$)$_2$); 2.71 ppm (2H, mc, Et-H$^1$); 3.16 ppm (2H, mc, CH$_2$-Ph); 3.25 ppm (4H, mc, morpholine-N—CH$_2$); 3.63 ppm (9H, s, Si(OCH$_3$)$_3$); 3.85 ppm (4H), mc, morpholine-O-CH$_2$); 6.61 ppm (1H, dd, Ph-H$^5$, $^3J_{H^5,H^6}$=8.6 Hz, $^4J_{H^3,H^6}$=2.6 Hz); 6.75 ppm (1H, d, Ph-H$^3$); 7.14–7.29 ppm (5H, m, Ph'-H); 8.44 ppm (1H, d, Ph-H$^6$).

EXAMPLE 10

Preparation of 2-benzyl-2-dimethylamino-1-|2-(2-triethoxysilylethyl)-4-morpholinophenyl|-1-butanone (10)

14.6 g (40 mmol) of 2-benzyl-2-dimethylamino-1-(4-morpholinophenyl)-1-butanone, 750 mg (0.8 mmol) of $RuH_2(CO)$ $(PPh_3)_3$ and 18.4 ml (88 mmol) of vinyltriethoxysilane were dissolved in 50 ml of toluene and degased using argon. After heating for 29 hours with stirring at reflux, the solvent was distilled off and the product was chromatographed (silica gel, heptane/$CH_2Cl_2$/ethyl acetate). 22 g (100%) of a brown oil were obtained which were purified by boiling in heptane with active charcoal followed by filtration to give a yellow, viscous oil in a quantity of 20.6 g (95%). $^1$H-NMR ($CDCl_3$): 0.64 ppm (3H, t, Bu-H$^4$, $^3J_{H,H}$=7.0 Hz); 1.10 ppm (2H, mc, Et-H$^2$); 1.26 ppm (9H, t, CH$_3$ of Si(OEt)$_3$, $^3J_{H,H}$=6.8 Hz); 1.88 ppm (2H, mc, Bu-H$^3$); 2.36 ppm (6H, s, N(CH$_3$)$_2$); 2.72 ppm (2H, mc, Et-H$^1$); 3.15 ppm (2H, mc, CH$_2$-Ph); 3.24 ppm (4H, mc, morpholine-N-CH$_2$); 3.85 ppm (4H, mc, morpholine-o—CH$_2$); 3.88 ppm (6H, q, SiOCH$_2$); 6.60 ppm (1H, dd, Ph-H$^5$, $^3J_{H^5,H^6}$=8.6 Hz, $^4J_{H^3, H^6}$=2.6 Hz); 6.77 ppm (1H, d, Ph-H$^3$); 7.12–7.28 ppm (5H, m, Ph'-H); 8.38 ppm (1H, d, Ph-H$^6$).

EXAMPLE 11

Preparation of 2-benzyl-2-dimethylamino-1-[2-(2-trimethoxysilylpropyl)-4-morpholinophenyl|-1-butanone (11)

5.49 g (15 mmol) of 2-benzyl-2-dimethylamino-1-(4-morpholinophenyl)-1-butanone, 275 mg (0.3 mmol) of $RuH_2(CO)$ $(PPh_3)_3$ and 5 g (30 mmol) of allyltrimethoxysilane were dissolved in 20 ml of toluene and degased with argon. After heating for 5 hours at reflux with stirring, the mixture was left to stand overnight, stirred at reflux for a further 9 hours, and again left to stand at room temperature. 280 mg (0.3 mmol) of $RuH_2(CO)$ $(PPh_3)_3$ were added and the mixture was boiled for 9 hours; it was then again left to stand overnight. 260 mg (0.3 mmol) of $RuH_2(CO)(PPh_3)_3$ were added, and the whole mixture was boiled again for 9 hours. After the solvent had been distilled off, the product was chromatographed (silica gel, heptane/$CH_2Cl_2$/ethyl acetate) and finally, by means of gel permeation chromatography (Sephadex LH-20, methanol) a pure fraction of 0.33 g (4%) of (11) was obtained as a yellow oil. $^1$H-NMR ($CDCl_3$): 0.68 ppm (3H, t, Bu-H$^4$, $^3J_{H,H}$=7.2 Hz); 0.77 ppm (mc, 2H, Prop-H$^3$); 1.64–1.96 ppm (4H, m, Bu-H$^3$ and Prop-H$^2$); 2.38 ppm (6H, s, N(CH$_3$)$_2$); 2.64 ppm (2H, mc, Prop-H$^1$); 3.16 ppm (2H, mc, CH$_2$-Ph); 3.24 ppm (4H, mc, morpholine-N —CH$_2$); 3.57 ppm (9H, s, Si(OCH$_3$)$_3$); 3.85 ppm (4H, mc morpholine-O-CH$_2$); 6.61 ppm (1H, dd, Ph-H$^5$, $^3J_{H^5,H^6}$=8.6 Hz); 6.72 ppm (1H, d, Ph-H$^3$, $^4J_{H^3,H^5}$=2.4 Hz); 7.13–7.25 ppm (5H, m, Ph'-H); 8.38 ppm (1H, d, Ph-H$^6$).

EXAMPLE 12

Preparation of 1-(2-trimethoxysilylethyl) thioxanthone (12) and 1,8-bis-(2-trimethoxysilylethyl)thioxanthone (13)

4.24 g (20 mmol) of thioxanthone, 360 mg (0.4 mmol) of $RuH_2(CO)$ $(PPh_3)_3$ and 2.36 ml (22 mmol) of vinyltrimethoxysilane were boiled at reflux in 30 ml of toluene for 6 hours. Following the addition of a further 230 mg (0.25 mmol) of $RuH_2(CO)$ $(PPh_3)_3$, the reaction solution was left to cool, and was separated off from the precipitated thioxanthone. After the solution had been concentrated, the product mixture was chromatographed (silica gel, $CH_2Cl_2$/ethyl acetate mixtures). Two fractions were obtained:

1.3 g (18%) of 12 (yellow oil), which was purified further by bulb-tube distillation. $^1$H-NMR ($CDCl_3$): 1.13 ppm (2H, mc, Et-H$^2$); 3.37 ppm (2H, mc, Et-H$^1$); 3.65 ppm (9H, s, Si(OCH$_3$)$_3$); 7.28 ppm (1H, mc)+7.39–7.46 ppm (3H, m)+7.48–78.52 ppm (1H, mc)+7.55 ppm (1H, mc)=H$^{2-7}$ and 8.46 ppm (1H, mc, H$^8$), and 1.77 g (17%) of 13, which after bulb-tubed distillation gave a crystalline, yellow mass. $^1$H-NMR ($CDCl_3$): 1.17 ppm (4H, mc, Et-H$^2$); 3.17 ppm (4H, mc, Et-H$^1$); 3.62 ppm (18H, s, Si(OCH$_3$))$_3$); 7.27 ppm (2H, mc)+7.32–7.43 ppm (4H, m)=H$^{2-7}$.

EXAMPLE 13

Preparation of 2-isopropyl-8-(2-trimethoxysilylethyl)-thioxanthone (14) and 2-isopropyl-1,8-bis-(2-(2-trimethoxy-silylethyl) thioxanthone 10.17 g (40 mmol) of 2-isopropylthioxanthone, 735 mg (0.8 mmol) of $RuH_2(CO)(PPh_3)_3$ and 6.72 ml (44 mmol) of vinyltrimethoxysilane in 50 ml of toluene were degased by passing in N$_2$. After boiling at reflux for 24 hours, the mixture was concentrated and chromatographed (silica gel, $CH_2Cl_2$/ethyl acetate mixtures). 2 fractions were obtained:

9.8 g (61%) of 14 as a yellow oil. $^1$H-NMR ($CDCl_3$): 1.15 ppm (2H, mc, Et-H$^2$); 1.32 ppm (6H, d, isopropyl-CH$_3$, $^3J_{H,H}$=6.6 Hz); 3.04 ppm (1H, hept., isopropyl-H$^2$); 3.38 ppm (2H, mc, Et-H$^1$); 3.65 ppm (9H, s, Si(OCH$_3$)$_3$); 7.27 ppm (1H, mc)+7.40–7.49 ppm (4H, m)=H$^{3-7}$; 8.34 ppm (1H, s(br.), H$^1$) and 1.37 g (6%) of 15 as a yellow oil. $^1$H-NMR ($CDCl_3$): 1.16+1.18 ppm (4H, mc in each case, Et-H$^2$); 1.32 ppm (6H, d, isopropyl-CH$_3$, $^3J_{H,H}$=6.6 Hz); 3.10+3.16 ppm (4H, mc, Et-H$^1$); 3.40 ppm (1H, hept., isopropyl-H$^2$); 3.61 ppm (18H, s, Si(OCH$_3$)$_3$); 7.25–7.44 ppm (5H, m, H$^{3-7}$).

EXAMPLE 14

Preparation of 2-benzyl-2-dimethylamino-1-|2-(2-(methylbis(trimethylsilyloxy)silyl)-ethyl)-4-morpholinophenyl|-1-butane (16)

8.1 g (22 mmol) of 2-benzyl-2-dimethylamino-1-(4-morpholinophenyl)1-butanone, 370 mg (0.4 mmol) of $RuH_2$ (CO) $(PPh_3)_3$ and 5.0 g (20 mmol) of vinylmethylbis (trimethylsilyloxy)silane were dissolved in 30 ml of toluene and degased using N$_2$. After heating at reflux with stirring for 48 hours, the solvent was distilled off and the residue was chromatographed (silica gel, heptane/ ethyl acetate). 4.9 g (40%) of a viscous, pale reddish oil were obtained. $^1$H-NMR ($CDCl_3$): 0.09 ppm (3H, s, Si-CH$_3$); 0.11 ppm (18H, s, Si(CH$_3$)$_3$); 0.65 ppm (3H, t, Bu-H$^4$); 0.89 ppm (2H, mc, Et-H$^2$); 1.87 ppm (2H, mc, Bu-H$^3$); 2.35 ppm (6H, s, N(CH$_3$)$_2$); 2.65 ppm (2H, mc, Et-H$^1$); 3.16 ppm (2H, mc, CH$_2$-Ph'); 3.24 ppm (4H, mc, morpholine-N-CH$_2$); 3.85 ppm (4H, mc, morpholine-o—CH$_2$); 6.59 ppm (1H, dd, Ph-H$^5$, $^3$J$_{H^5,H^6}$=8.4 Hz); 6.73 ppm (1H, d, Ph-H$^3$, $^4$J$_{H^3,H^5}$=2.6 Hz); 7.12–7.28 ppm (5H, m, Ph'-H); 8.35 ppm (1H, d, Ph-H$^6$).

EXAMPLE 15

Reaction of a dimethylsiloxane-vinyl-methylsiloxane copolymer with 2-benzyl-2-dimethylamino-1-(4-morpholinophenyl)-1-butanone to give compound (17)

13.7 g (37.4 mmol) of 2-benzyl-2-dimethylamino-1-(4-morpholinophenyl)-1-butanone, 0.69 g (0.75 mmol) of RuH$_2$(CO) (PPh$_3$)$_3$ and 25 g of a dimethylsiloxane-vinylmethylsiloxane copolymer (7.5% vinylmethyl units, $n$ =1000 mm$^2$/s) were dissolved in 30 ml of toluene, degased using nitrogen and heated at reflux with stirring for 100 hours. After concentrating the mixture, taking up the residue in heptane, applying this mixture to silica gel and carrying out elution with about 500 ml of heptane, 24.8 g of a pale reddish oil were isolated whose $^1$H-NMR spectrum corresponds to that of a polydimethylsiloxane featuring comb-like substitution. On the basis of the spectrum, 68% of the vinyl radicals originally present had been replaced by 2-[2-(2-benzyl-2- dimethylaminobutanoyl)-5-morpholinophenyl] ethyl radicals. Further purification is possible by boiling up with active charcoal.

EXAMPLE 16

Reaction of a polydimethylsiloxane containing terminal vinyldimethylsilyl groups with 2-benzyl-2-dimethylamino-1- (4-morpholinophenyl) -1-butanone to give (18)

16.1 g (44 mmol) of 2-benzyl-2-dimethylamino-1-(4-morpholinophenyl)-1-butanone, 367 mg (0.4 mmol) of RuH$_2$(CO) (PPh$_3$)$_3$ and 9.1 g of a polydimethylsiloxane containing terminal vinyldimethylsilyl groups ($n$=4–6 mm$^2$/s) were dissolved in 50 ml of toluene and degased using nitrogen. After heating at reflux with stirring for 52 hours, the mixture was worked up by chromatography. 9.3 g of a reddish oil of (18) were isolated whose $^1$H-NMR spectrum corresponded to that of a terminally substituted polydimethylsiloxane, which spectrum showed virtually no remaining vinyl terminal groups and instead exhibited the signals typical of 2-[2-(2-benzyl-2-dimethylaminobutanoyl) -5-morpholinophenyl]ethyl radicals (cf. Compounds 9 and 10).

EXAMPLE 17

Use of photoinitiators substituted by trialkoxysilylalkyl radicals for the condensation curing of silicones A stock solution was prepared from 20.0 g of toluene, 5 g of a 33% strength solution of an Si—OH-containing polydimethylsiloxane in toluene and 0.1 g of an organometallic crosslinking catalyst based on tin. 75 (±5) mg of the compound according to the present invention indicated in Table 4 were added to 2.5 g portions of this stock solution, and the mixtures were knife-coated using a drawing rod onto a polyester film and cured for 2 minutes at 105° C. in a convection oven. The properties of the silicone rubbers obtained in this process, together with the optical properties of the substituted photoinitiators shown, are compiled in the following table. If lower concentrations of photoinitiator according to the present invention are used than in the examples, clear silicone films are obtained.

TABLE 4

Optical spectra of the various photoinitiator derivatives and properties in relation to the condensation crosslinking of silicones

| Compound Number | Condensation crosslinking | Properties of the crosslinked silicone | optical properties[b] |
|---|---|---|---|
| 1 | yes | hazy, milky, abrasion-resistant | 329 (shoulder) |
| 2 | yes | hazy, slightly milky, almost abrasion-resistant | 325 (shoulder) |
| 3 | yes | hazy, colorless, not totally abrasion-resistant | 325 (shoulder) |
| 4 | partially | clear, colorless, slightly greasy, curing incomplete[c] | 325 (shoulder) |
| 5 | yes | clear, colorless, abrasion-resistant | 328 (shoulder) |
| 6 | yes | hazy, slightly milky, not entirely abrasion-resistant | 271 (shoulder) |
| 7 | n.d.[a] | | 293 (12400) |
| 8 | n.d. | | |
| 9 | yes | hazy, milky, almost abrasion-resistant | 312 (15400) |
| 10 | yes | clear, yellowish, abrasion-resistant[d] | 311 (15800) |
| 11 | n.d. | | |
| 12 | yes | hazy, milky, abrasion-resistant | 380 (5760) 259 (35900) |
| 13 | yes | hazy, milky, abrasion-resistant | 375 (4660) 260 (35600) |
| 14 | n.d. | | 385 (6180) 261 (41200) |
| 15 | n.d. | | 376 (5400) 260 (37800) |

[a] not determined
[b] λ$_{max}$[nm]; ε[l · mol$^{-1}$ cm$^{-1}$] of the compounds according to the invention in CH$_2$Cl$_2$
[c] incomplete curing, drying time too short
[d] crosslinking with a smaller proportion of trioxysilane derivative

EXAMPLE 18

Covalent fixing of trialkoxysilylalkylsubstituted photoinitiators in the condensation curing of silicones a) A solution of 13.5 g of toluene, 4.5 g of the polydimethylsiloxane solution in toluene indicated in Example 17, 0.1 g of a 50% strength solution of 2-benzyl-2-dimethylamino-1-[2-(2-triethoxysilylethyl)-4-morpholinophenyl]-1-butanone (10) and 0.12 g of the crosslinking catalyst indicated in Example 17 was poured into a glass dish and cured at 120° C. for 5 minutes. The clear silicone rubber obtained was extracted for 3 hours with dichloromethane. The extract was found by UV/Vis spectroscopy to contain 34% of the photoinitiator employed.

b) The experiment described in a) was repeated but using instead of compound (10), 2-benzyl-2-dimethylamino-1-[2-(2-trimethoxysilylethyl)-4-morpholinophenyl]-1-butanone (9) was used. The clear silicone rubber obtained was extracted with dichloromethane for 3 hours. The extract was found by UV/Vis spectroscopy to contain 2% of the photoinitiator employed.

EXAMPLE 19

Use of 2-benzyl-2-dimethylamino-1-[2-(2-triethoxysilylethyl)-4-morpholinophenyl]-1-butanone (10) as photoinitiator in a photopolymer mixture

TABLE 5

Composition of the solutions used and photosensitivity of the films obtained

| | Solution 1 (g) | Solution 2 (g) |
|---|---|---|
| Solution of poly(methacrylic acid-co-methyl methacrylate) (acid number 117) in butanone (33.2%) | 3.03 | 3.01 |
| Tetrahydrofuran | 3.03 | 3.01 |
| Hydroquinone | 0.012 | 0.010 |
| Pentaerythritol triacrylate | 2.02 | 2.03 |
| (10) (50% strength solution in toluene) | 0.149 | — |
| [2-Benzyl-2-dimethylamino-1-(4-morpholinophenyl)-1-butanone] | — | 0.155 |
| | Wedge steps | |
| Duration of exposure 50 s | 1 | 3 |
| Duration of exposure 100 s | 3 | 6–7 |
| Duration of exposure 200 s | 5 | 8 |

An aluminum panel was coated with solutions 1 and 2 using a doctor knife, each of the layers was dried over 100° C. for 2 minutes, a biaxially oriented and heat-set polyester film (23 μm) was laminated onto the layer at a roll temperature of 100° C., and this laminate was exposed under a standard step wedge (Ugra wedge) with a high-pressure mercury lamp, with variation of the exposure time (see Table 5). Development is carried out after peeling off the film by rubbing off with ethyl acetate. Table 5 indicates the first completely cured wedge step in each case.

EXAMPLE 20

Use of 2-benzyl-2-dimethylamino-1-[2-(2-triethoxysilylethyl)-4-morpholinophenyl]-1-butanone (10) for the production of a printing plate A solution of 6.0 g of the methacrylic acid copolymer solution indicated in Example 19, 8.0 g of tetrahydrofuran, 1.6 g of pentaerythritol triacrylate and 0.1 g of hydroquinone was applied to an aluminum plate using a doctor knife, and the film was dried for 2 minutes at 105° C. in a convection oven. A solution of 13.56 g of toluene, 4.27 g of the polydimethylsiloxane solution indicated in Example 17, 0.88 g of a silicone containing lateral acrylic acid groups, 0.09 g of hydroquinone monomethyl ether, 0.16 g of the crosslinking catalyst indicated in Example 17, 0.12 g of Renol blue B2G (C. I. 74160) and 1.12 g of a 33% solution of (10) in toluene was coated onto a 10 μm thick polyethylene film using a doctor knife, and the film was cured for 3 minutes at 105° C. in a convection oven. The film coated in this way was laminated at 100° C. onto the aluminum support coated with the photopolymer solution. Following exposure with a high-pressure mercury lamp, the film was peeled off. In the exposed regions, the silicone adhered to the photopolymer film, while in the unexposed regions it was separated with the film from the photopolymer layer. Accordingly, the exposed regions were ink-repellent while the unexposed regions accepted printing ink.

Other embodiments of the invention will be apparent to those skilled in the art from consideration of the specification and practice of the invention disclosed herein. It is intended that the specification be considered as exemplary only, with the true scope and spirit of the invention being indicated by the following claims.

What is claimed is:

1. A compound which forms radicals when irradiated with actinic radiation of the formula I $$(SIL-X-)_m IN \qquad (I),$$

in which

SIL is a radical of the formula $Si(R^1)(R^2)(R^3)$, where $R^1$ is selected from the group consisting of an alkyl, haloalkyl or alkoxy radical of 1 to 8 carbon atoms, an alkenyl radical, an alkenyloxy or acyloxy radical of 2 to 8 carbon atoms, an aryl or aryloxy radical of 6 to 10 carbon atoms, or a dialkyl-, diaryl- or alkylarylmethyleneaminooxy radical having $C_1$–$C_4$-alkyl or $C_6$-aryl groups, and $R^2$ and $R^3$ are identical or different radicals with the meaning of $R^1$ or X—IN, X is a group $C_n H_{2n}$.

IN is the radical of a compound which has one or more of a photoinitiator or photosensitizer activity and which has at least one carbonyl group located on an aromatic nucleus, m is a number from 1 to 4, and n is a number from 2 to 12, or a compound of the formula II $$SiO_o O_{o-1}(-X-IN)_p R^4_{2o+2-p} \qquad (II)$$

in which $R^4$ is a radical with the meaning of $R^1$, and two or more radicals $R^4$ are identical or different from one another, o is a number from 2 to 20,000, and p is a number from 1 to o, wherein the symbols X and IN are defined as above, and wherein the group X is attached to an aromatic carbon atom which is positioned ortho to the carbonyl group of IN.

2. A compound as claimed in claim 1, wherein

IN is a radical of one of the formulae V and VI in which $R^5$, $R^6$ and $R^7$ are identical or different and are selected from the group consisting of hydrogen atoms, halogen atoms, phenyl, benzyl or benzoyl radicals, alkyl radicals of 1 to 12 carbon atoms, cycloalkyl radicals of 5 to 6 carbon atoms or radicals of the formulae $OR^{12}$, $SR^{12}$, $SOR^{15}$, $SO_2R^{15}$, $N(R^{13})(R^{14})$, $NH-SO_2-R^{15}$ and $NHCOR^{15}$.

$R^8$ and $R^9$ are identical or different and are selected from the group consisting of hydrogen atoms, alkyl radicals of 1 to 12 carbon atoms, alkenyl radicals of 2 to 12 carbon atoms, 5- or 6-membered cycloalkyl

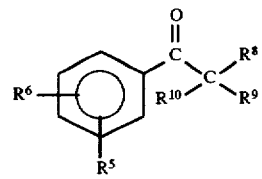

-continued

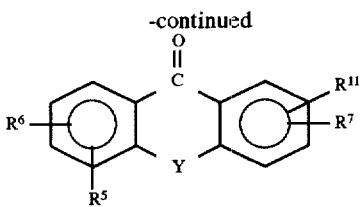
(VI)

radicals, aralkyl radicals of 7 to 9 carbon atoms, $OR^{12}$, $CH_2OR^{12}$ or $N(R^{13})(R^{14})$, or $R^8$ and $R^9$ together with the carbon atom to which they are attached form a cycloaliphatic ring of 5 to 6 carbon atoms; and $R^{10}$ is a hydrogen atom, $OR^{12}$ or an aryl radical of 6 to 8 carbon atoms, or, alternatively, $R^8$, $R^9$ and $R^{10}$ together with the carbon atom to which they are attached form a substituted or unsubstituted benzene ring, $R^{11}$ is X—SIL in position 1 of the triple-ring system of the formula VI or $R^7$, $R^{12}$ is selected from the group consisting of a hydrogen atom, an alkyl radical of 1 to 12 carbon atoms, a 5- or 6-membered cycloalkyl radical or an alkanoyl radical of 2 to 13 carbon atoms, $R^{13}$ and $R^{14}$ are identical or different and are hydrogen atoms, alkyl radicals of 1 to 12 carbon atoms or 5- or 6-membered cycloalkyl radicals, or $R^{13}$ and $R^{14}$ together with the nitrogen atom to which they are attached form a 5- or 6-membered heterocyclic ring which optionally contains O, S or N as additional heteroatoms, $R^{15}$ is an alkyl radical of 1 to 12 carbon atoms or an aryl radical of 6 to 10 carbon atoms, and Y is selected from the group consisting of O, S, $NR^{12}$, $CH_2$, C(O) or a single bond, and if Y=C(O) radicals X—SIL are optionally also present in positions 4 and 5 of the triple-ring system.

3. A compound as claimed in claim 2, wherein IN is a radical of formula V, and wherein at least one of $R^5$ and $R^6$ is selected from the group consisting of H, alkyl-, alkoxy- or alkylmercapto of 1 to 4 carbon atoms, $N(R^{13})(R^{14})$ with alkyl radicals $R^{13}$ and $R^{14}$ of 1 to 4 carbon atoms, or wherein $N(R^{13})(R^{14})$ form a 5 or 6 membered heterocyclic ring.

4. A compound as claimed in claim 2, wherein one of $R^5$ and $R^6$ is a hydrogen atom and the other of $R^5$ and $R^6$ is $N(R^{13})(R^{14})$ which forms a 5 or 6 membered heterocyclic ring, and wherein the heterocyclic ring contains O, S or NH as additional heteroatoms.

5. A compound as claimed in claim 2, wherein at least one of radicals $R^8$ and $R^9$ is an alkyl or alkoxy group of 1 to 4 carbon atoms, wherein not more than one of $R^8$ and $R^9$ is a hydrogen atom, a hydroxy or an aralkyl groups and wherein $R^{10}$ is a substituted or unsubstituted phenyl radical, a hydroxyl group or a tertiary linear or cyclic amino group.

6. A compound as claimed in claim 2, wherein $R^8$, $R^9$ and the carbon atom to which they are attached form a cycloaliphatic ring if 5 or 6 carbon atoms.

7. A compound as claimed in claim 2, wherein $R^8$, $R^9$ and $R^{10}$ and the carbon atom to which they are attached form a benzene ring.

8. A compound as claimed in claim 2, wherein IN is a radical of the formula VI, and one or more of $R^5$, $R^6$ and $R^7$ are hydrogen atoms.

9. A compound as claimed in claim 2, wherein one or two of $R^5$, $R^6$ and $R^7$ are halogen atoms, alkyl groups of 1 to 4 carbon atoms or tertiary amino groups of 2 to 6 carbon atoms.

10. A compound as claimed in claim 2, wherein Y is O, S, NH or CO.

11. A compound as claimed in claim 1, wherein $R^1$ and $R^2$ are alkyl or alkoxy groups of 1 to 4 carbon atoms.

12. A compound as claimed in claim 1, wherein the ratio of p:o is between 1:100 and 1:2.

13. A compound as claimed in claim 1, wherein $R^4$ is an alkyl group of 1 to 4 carbon atoms.

14. A compound as claimed in claim 1, wherein X is an alkylene group having 2 to 6 carbon atoms.

15. A compound as claimed in claim 1, wherein the compound is selected from the group consisting of:
2-[2-(Trimethoxysilyl)ethyl]benzoin methyl ether,
2-[2-(Trimethoxysilyl)ethyl]benzoin ethyl ether,
2-[2-(Trimethoxysilyl)ethyl]benzoin isopropyl ether,
2-[2-(Triethoxysilyl)ethyl]benzoin isopropyl ether,
2-[2-(Trimethoxysilyl)ethyl]benzil dimethyl ketal,
1-Hydroxy-1-[2-(2-trimethoxysilylethyl)benzoyl] cyclohexane,
2-Methyl-1-[4-methylthio-2-(2-trimethoxysilylethyl) phenyl]-2-morpholino-1-propanone,
2-Methyl-1-[4-methylthio-2-(2-triethoxysilylethyl)phenyl]-2-morpholino-1-propanone,
2-Benzyl-2-dimethylamino-1-[2-(2-trimethoxysilylethyl)-4-morpholinophenyl]-1-butanone,
2-Benzyl-2-dimethylamino-1-[2-(2-triethoxysilylethyl)-4-morpholinophenyl]-1-butanone,
2-Benzyl-2-dimethylamino-1-[2-(2-trimethoxysilylpropyl)-4-morpholinophenyl]-1-butanone,
1-(2-Trimethoxysilylethyl)thioxanthone,
1,8-Bis-(2-trimethoxysilylethyl)thioxanthone,
2-Isopropyl-8-(2-trimethoxysilylethyl)thioxanthone,
2-Isopropyl-1,8-bis-(2-trimethoxysilylethyl)thioxanthone,
2-Benzyl-2-dimethylamino-1-[2-(2-(methyl-bis (trimethylsilyloxy) silyl)ethyl) -4-morpholinophenyl]1-butanone,
Siloxane copolymer comprising dimethylsiloxane, methylvinylsiloxane and {2-[2-(2-benzyl-2-dimethylaminobutanoyl)-5-morpholinophenyl] ethyl}methylsiloxane units, and
2-[2-(2-Benzyl-2-dimethylaminobutanoyl)-5-morpholinophenyl]phenyl]ethyl-terminated polydimethylsiloxane.

16. A process for the preparation of a compound of the formula I or II as claimed in claim 1, which comprises reacting a compound of the formula III

IN—H (III)

in which the hydrogen atom is on an aromatic carbon atom positioned ortho to a carbonyl group, in the presence of a catalytic amount of a ruthenium compound, with a compound of the formula IV

SIL—X' (IV)

or a compound of the formula IVA $Si_oO_{o-1}(—X')_pR^4{}_{2o+2-p}$ (IVA)

in which X' is an ω-alkenyl radical of 2 to 12 carbon atoms and IN, SIL, R⁴, o and p are as defined in claim 1.

17. The process as claimed in claim 16, wherein the reaction is carried out at a temperature between 100° C. and 180° C.

18. The process as claimed in claim 16, wherein the reaction is carried out in an organic solvent selected from the group consisting of benzene, toluene, xylene and chlorobenzene.

19. A photosensitive mixture comprising a) a polysiloxane, b) a free-radically polymerizable compound having at least one terminal ethylenically unsaturated group, and c) a compound as claimed in claim 1 which forms radicals when irradiated with actinic radiation.

20. A photosensitive mixture as claimed in claim 19, further comprising one or more of crosslinking catalysts, additional photocatalysts, inhibitors, heat stabilizers, light stabilizers, photosensitizers, colorants, fillers and solvents.

21. A two-stage process for curing silicone, comprising crosslinking silicone resins which contain at least one of the compounds according to claim 1 by a condensation reaction to produce a silicone rubber, and further polymerizing the silicone rubber by exposure to actinic radiation.

* * * * *

UNITED STATES PATENT AND TRADEMARK OFFICE
CERTIFICATE OF CORRECTION

PATENT NO. : 5,776,658
DATED : July 7, 1998
INVENTOR(S) : Claus-Peter NIESERT et al.

It is certified that error appears in the above-identified patent and that said Letters Patent is hereby corrected as shown below:

Please note that Column 19, Claim 5, line 4, contains typographical errors wherein "hydroxy or an aralkyl groups" should read --hydroxy or aralkyl group--; Claim 6, line 3, "if 5 or 6 carbon atoms" should read --of 5 or 6 carbon atoms--. Column 20, Claim 15, line 32 incorrectly recites "morpholinophenyl]phenyl]ethyl-terminated" this claim should read --morpholinophenyl]ethyl-terminated--.

Signed and Sealed this

Twenty-sixth Day of October, 1999

Attest:

Q. TODD DICKINSON

Attesting Officer      Acting Commissioner of Patents and Trademarks